United States Patent [19]

Inoue

[11] Patent Number: 5,233,416
[45] Date of Patent: Aug. 3, 1993

[54] ELECTRONIC ENDOSCOPE SYSTEM
[75] Inventor: Kiyoshi Inoue, Omiya, Japan
[73] Assignee: Fuji Photo Optical Co., Ltd., Omiya, Japan
[21] Appl. No.: 906,489
[22] Filed: Jun. 30, 1992
[30] Foreign Application Priority Data Jul. 1, 1991 [JP] Japan .................................. 3-185825

[51] Int. Cl.$^5$ .......................... A61B 1/04; A61B 1/06; H04N 7/18
[52] U.S. Cl. ........................................ 358/98; 358/42
[58] Field of Search ........................ 358/98, 42; 128/6

[56] References Cited

U.S. PATENT DOCUMENTS

| | | | |
|---|---|---|---|
| 4,851,899 | 7/1989 | Yoshida | 358/42 |
| 4,926,258 | 5/1990 | Sasaki | 358/98 |
| 5,006,928 | 4/1991 | Kawajiri | 358/98 |
| 5,103,300 | 4/1992 | Nitta | 358/42 |

*Primary Examiner*—Tommy Chin
*Assistant Examiner*—Bryan S. Tung
*Attorney, Agent, or Firm*—Oblon, Spivak, McClelland, Maier & Neustadt

[57] ABSTRACT

An electronic endoscope system compatible with solid-state image sensor elements of different types, including a rotary color wheel located in the path of illuminating light from a light source and provided with RGB filter zones successively and alternately with a color-shifting main light-blocking zone to transmit illuminating light rays of red, green and blue wavelength sequentially therethrough, and a light guide for directing the red, green and blue illuminating light rays from the color wheel toward an internal portion under observation, while picking up images of a subject under sequential irradiations by red, green and blue light rays from the light guide. Each one of the filter zones is bisected by an intermediate light blocking zone which is provided at a median point thereof. The electronic endoscope system further includes an image sensor drive which is operable either in a single-field drive mode where on each revolution of the color wheel signal charges are read out from the solid-state image sensor element only in main blank periods when a main light-blocking zone with a color shift is in the path of illuminating light and a double-field drive mode where signal charges are read out from the solid-state image sensor element in both main and intermediate blank periods when a main or intermediate light-blocking zone is in the path of illuminating light to obtain two fields of picture data of each color on each revolution of the color wheel.

4 Claims, 7 Drawing Sheets

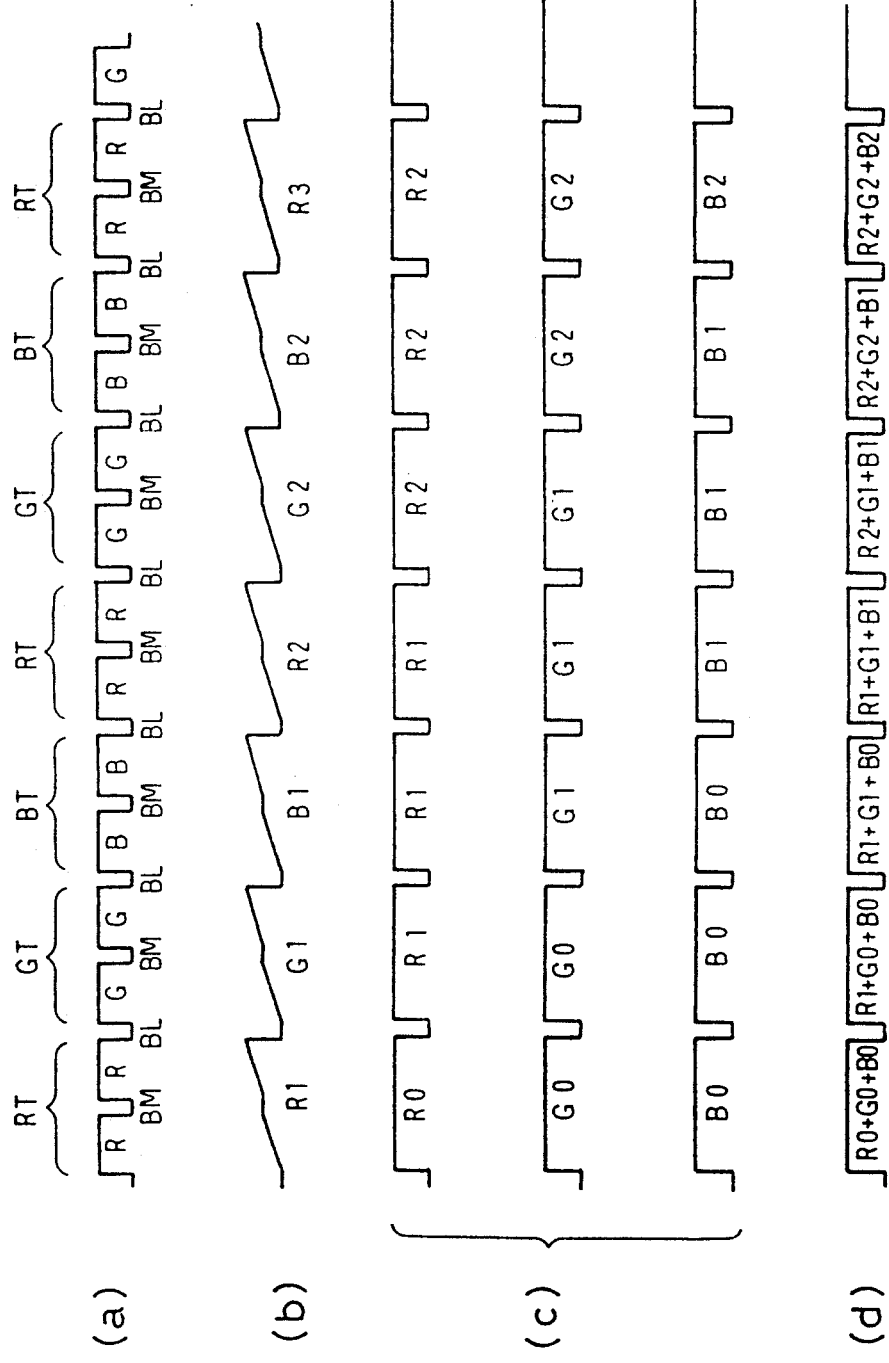

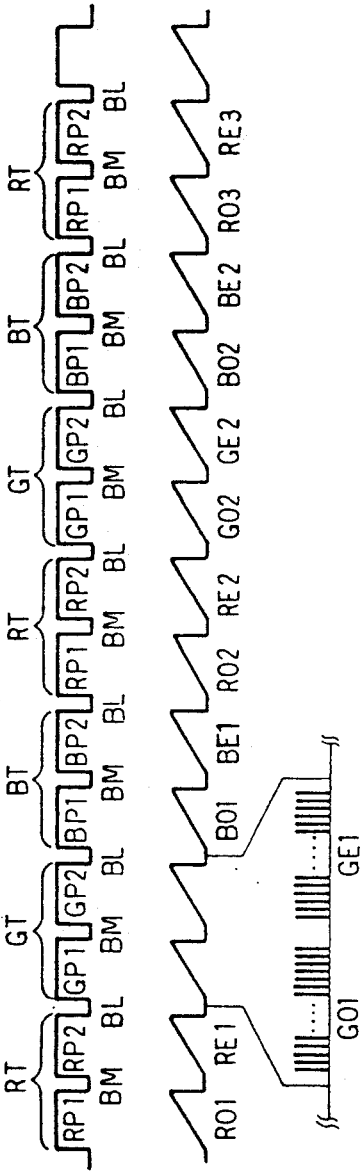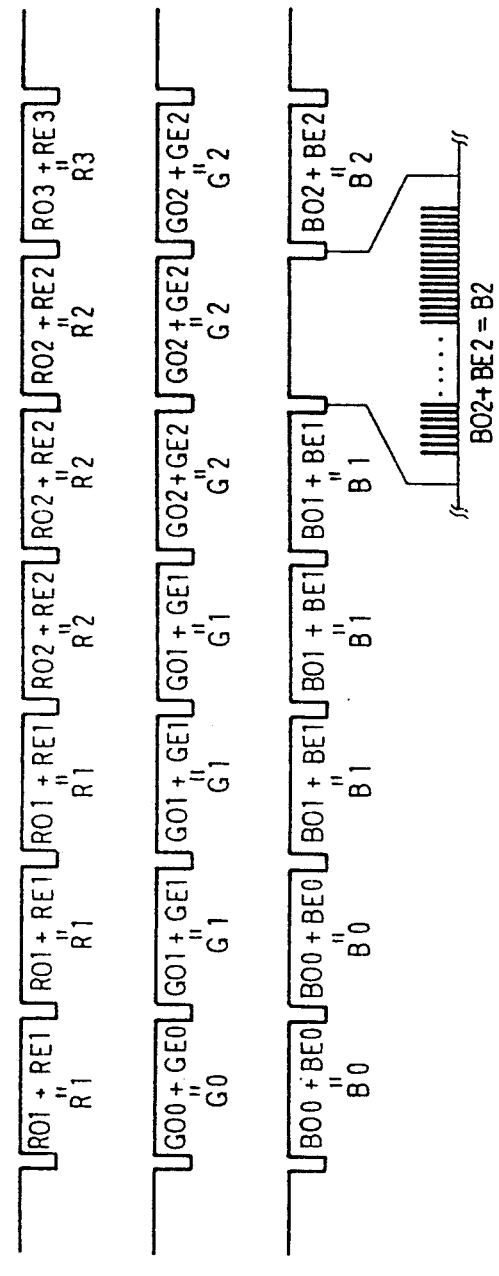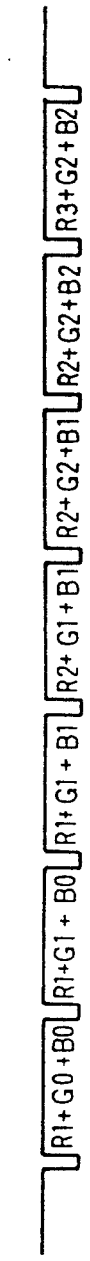
FIG. 5(a)
FIG. 5(b)
FIG. 5(c)
FIG. 5(d)

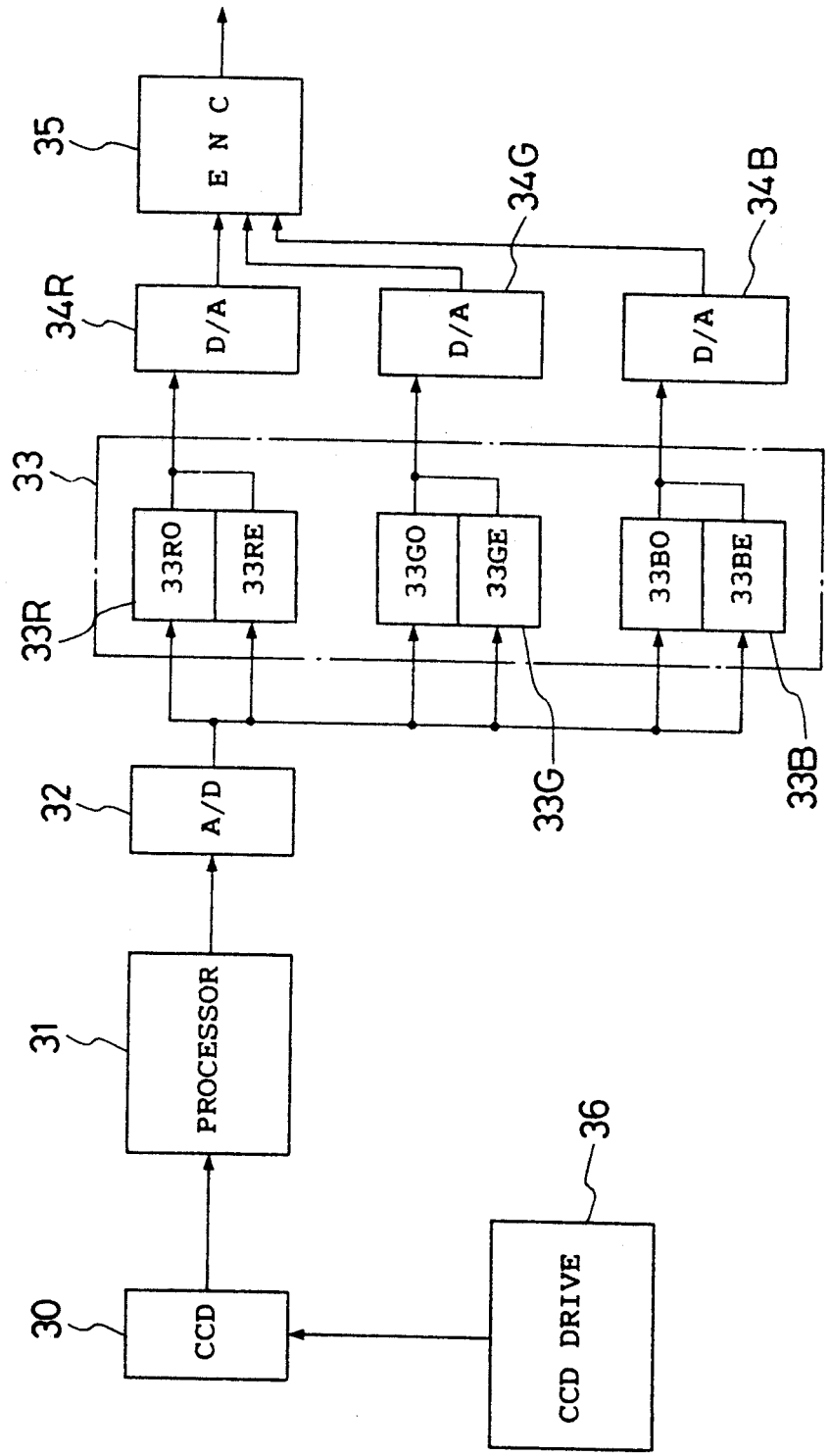

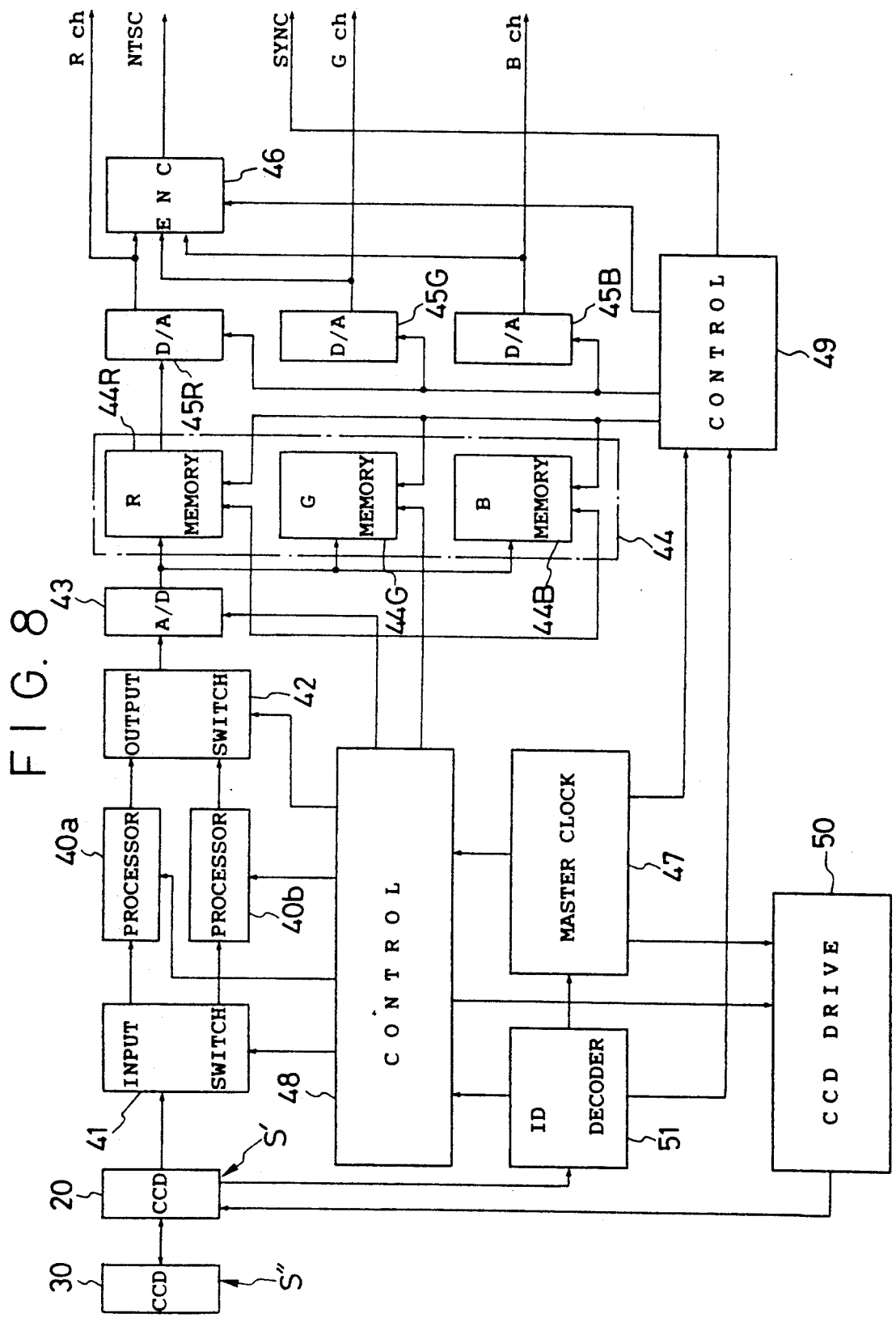

ELECTRONIC ENDOSCOPE SYSTEM

BACKGROUND OF THE INVENTION

1. Field of the Art

This invention relates to an electronic endoscope system suitable for applications in medical and industrial fields, and more particularly to an electronic endoscope system incorporating an image sensor drive compatible with solid-state image sensor elements of different classes in sensitivity.

2. Prior Art

The electronic endoscopes usually incorporate a solid-state image sensor element like CCD at the tip end of a catheter portion to be inserted into an internal portion of a human body or of a machine, thereby picking up images of an internal portion of interest and displaying its color images on a monitor screen for observation purposes.

In this connection, to cope with the darkness of intracorporeal or internal portions to be examined or diagnosed through the endoscope, the locality of interest which confronts the inserted tip end of the catheter portion is observed in an illuminated state. For this purpose, the endoscope is connected to a light source, and illuminating light rays from the light source are led through a light guide, which is coextensively provided in the catheter portion, and projected through an illumination window at the tip end of the catheter portion. Further, an observation window with an objective lens is provided also at the tip end of the catheter portion to focus the image of an intracorporeal portion under observation on a solid-state image sensor element through the objective lens. As well known in the art, the solid-state image sensor element has a multitude of pixels which accumulate signal charges when the image sensor is exposed to light. The accumulated signal charges in the respective pixels are sequentially read out in a predetermined timing and sent to a signal processing unit to obtain video signals.

In this connection, for an endoscopic image pickup system using a solid-state image sensor, it is the usual practice to adopt a single-element image sensor for the purpose of minimizing the diameter of the catheter portion of the endoscope. Besides, for improving the resolution of the picture images, the image sensor element is driven by a sequential color scan system which sequentially fetches the picture signals of red (R), green (G) and blue (B) fields. Generally, the field signals of these three colors are processed into a composite video signal thereby to display a color image on a monitor screen.

For these purposes, the illumination light rays projected from the light source through the light guide needs to change its spectral characteristics to irradiate an internal area of interest sequentially with light rays of R, G and B wavelengths. Further, for reading out the accumulated signal charges from the solid-state image sensor element, it is necessary to provide a blank period between the irradiation periods of the respective colors. To this end, the light source usually incorporates a color filter, including a color wheel which is located in the light path between a source lamp and an input end of the light guide, and a drive means which rotationally drives the color wheel. The color wheel is provided with a filter track containing a R-filter zone transmissive of light of red wavelength, a G-filter zone transmissive of light of green wavelength and a B-filter zone transmissive of light of green wavelength successively and alternately with a blank light-blocking zone.

When the color wheel is driven to rotate, picture signals of R field are accumulated in the solid-state image sensor element in a red irradiation period when the R-filter zone is in the path of the illuminating light, and these signals are read out in a succeeding blank period. Similarly, picture signals of G field are accumulated in a green irradiation period when the G-filter zone is in the illuminating light path, and read out in a succeeding blank period. Picture signals of B field are accumulated in the next blue irradiation period when the B-filter zone comes into the illuminating light path, and the accumulated signals are read out in a succeeding blank period. These operations are repeated cyclically to obtain video signals of the internal portion under observation.

In an actual image pickup operation using such a solid-state image sensor element, for example, the light rays of RGB wavelengths are successively and periodically projected from the light source at time intervals of 16.6 ms while exposing the solid-state image sensor to reflected light and reading out signal charges in each blank period when a light-blocking zone comes into the illumination light path. After signal processing, the read-out picture signals are stored in a field memory which is arranged to renew one of picture data of R, G or B field each time when new field data of the corresponding color are received. The renewed picture data of one color are read out from the field memory concurrently with previous field data of the other two colors, and converted into concurrent video signals by a color encoder. The output video signals of the color encoder consist of odd-numbered field signals and even-numbered field signals. In this regard, the endoscope solid-state image sensor element has storage portions which correspond approximately to ½ of the number of pixels in the light receiving areas in the vertical direction. Therefore, in reading out field data of one color, it is the usual practice to add up two pixels in the vertical direction by mixed pixel read-out.

Generally, when mixing two pixels in the vertical direction in connection with the interlacing action, an odd-numbered field signal or an even-numbered field signal is obtained by adding a preceding line or a succeeding line to each scanning line, permitting to reproduce a picture image by line interlacing on the basis of these two field signals. However, in case of an electronic endoscope, it has been the general practice to read out only one of these two field signals, for example, only the odd-numbered field signals.

Further, in consideration of insertion into intracavitary portions of human body, the catheter portion of the endoscope is desired to be as small as possible in diameter to ensure smooth passage through constricted portions and to lessen pains on the part of the patient. Therefore, the solid-state image sensor element like CCD to be incorporated into a tip end portion of the catheter as an image pickup means has been facing strong demands for reductions in size. In order to meet these demands by the use of a recently developed high-sensitivity solid-state image sensor element which has almost doubled sensitivity as compared with the conventional counterpart along with excellent dynamic range and RGB spectral sensitivity ratios, the present inventor proposed in his co-pending U.S. patent application Ser. No. 07/748,961 an electronic endoscope system capable of obtaining pictures of high quality from a solid-state image sensor element of a reduced size which is approximately halved in the number of pixels in the vertical direction as compared with the conventional counterpart and which is driven at a higher speed to produce two fields of picture data in the image pickup system within a period of one field in the image reproducing system.

In picking up an image of a subject, the high sensitivity image sensor element of this sort requires to repeat each of the RGB irradiations for a couple of times by the use of a color wheel of an arrangement different from the one which is usually used with an ordinary or normal sensitivity solid-state image sensor element. In this regard, since it is inconvenient and troublesome to change the light source according to the type of the solid-state image sensor element, the present inventor developed a rotary color filter which is provided with two or more filter tracks concentrically on a color wheel in such a way as to shift selected one of the filter tracks into a position in alignment with the path of illuminating light from the source lamp.

The rotary color filter of this arrangement can cope with a number of solid-state image sensors of different type, but needs to provide a wheel shifting means for moving the color wheel in a direction perpendicular to the illumination light path. The wheel shifting means is required to include not only a mechanism for shifting the color wheel position but also a mechanism for simultaneously shifting the position of a rotational drive motor for the color wheel, resulting in a substantial increase in size and complication of the rotary color filter construction as a whole.

SUMMARY OF THE INVENTION

The present invention contemplates to eliminate the above-mentioned problems or drawbacks of the conventional electronic endoscopes, and has as its object the provision of an improved electronic endoscope system which is adaptable to solid-state image sensor elements of different types by the use of a rotary color filter of simple construction.

In accordance with the present invention, the above-stated objective is achieved by the provision of an electronic endoscope system, essentially including: an illumination lamp; a rotary color wheel located in the path of illuminating light from the illumination lamp and formed with RGB filter zones successively and alternately with a color-shifting main light-blocking zone to transmit illuminating light rays of red, green and blue wavelengths sequentially therethrough, and an intermediate blocking zone provided at a median point of each one of the filter zones; a light guide adapted to guide illuminating light rays of red, green and blue of wavelengths from the color wheel sequentially to a subject under observation; a solid-state image sensor element for picking up images of the subject under sequential irradiations by red, green and blue light rays from the light guide; and a CCD drive circuit switchable to operate in a single-field drive mode where signal charges are read out from the image sensor element only at each main blank period when a color-shifting main light-blocking zone is in the path of illuminating light, skipping over the intermediate blank zones, and in a double-field drive mode where signal charges are read out from the image sensor element at each one of main and intermediate blank periods when a main or intermediate light-blocking zone is in the path of illuminating light, thereby obtaining two fields of picture data of each color on each revolution of the color wheel.

The above and other objects, features and advantages of the present invention will become apparent from the following description and the appended claims, taken in conjunction with the accompanying drawings showing some preferred embodiments of the invention, which are given for illustrative purposes only and, needless to say, should not be construed as limitative of the invention.

BRIEF DESCRIPTION OF THE DRAWINGS

In the accompanying drawings:

FIG. 4 shows various diagrams concerning a single-field drive type solid-state image sensor element, i.e., at (a) a diagram of RGB irradiation periods by illuminating light, at (b) a diagram of stored CCD signals corresponding to the irradiation periods, at (c) a diagram of output signals from a memory, and at (d) a diagram of output signals from a color encoder;

FIG. 5 shows various diagrams concerning a double-field drive type solid-state image sensor element, i.e., at (a) a diagram of RGB irradiation periods by illuminating light, at (b) a diagram of stored CCD signals corresponding to the irradiation periods, at (c) a diagram of output signals from a memory, and at (d) a diagram of output signals from a color encoder;

FIG. 7 is a circuit diagram of a video signal processor for the double-field drive type solid-state image sensor element; and FIG. 8 is a circuit diagram of a video signal processor with functions of handling signals from both of the single and double-field drive type solid-state image sensor elements.

DESCRIPTION OF PREFERRED EMBODIMENTS

Figure 1:
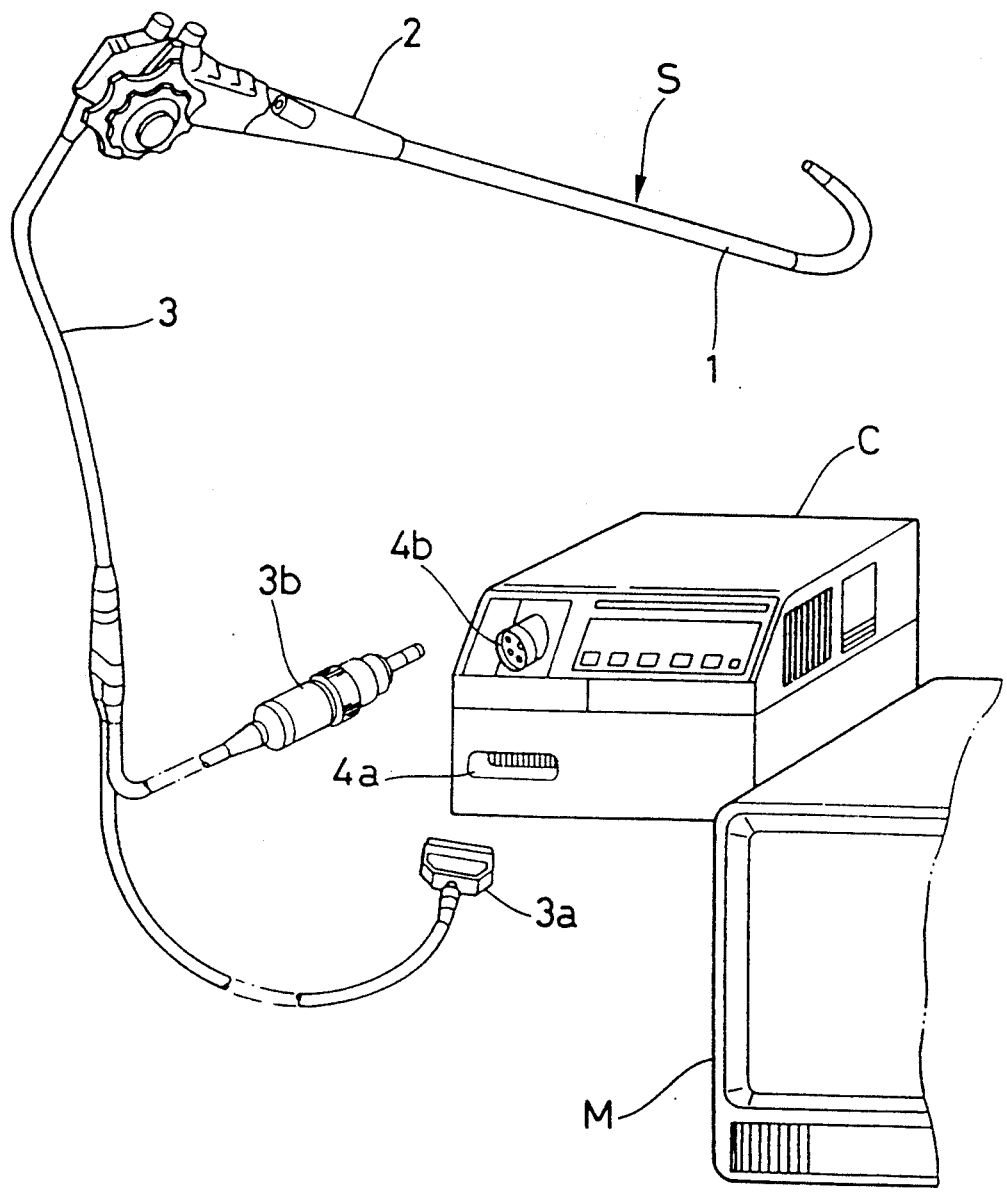
FIG. 1 is a general view of an electronic endoscope system to which the present invention is applicable.

Hereafter, the invention is described more particularly by way of preferred embodiments shown in the drawings.

Referring to FIG. 1, there is shown the general arrangement of an electronic endoscope system, which is, as clear from that figure, largely constituted by an endoscope S, a control unit C and a monitor M. The endoscope S includes a catheter portion 1 to be inserted into an internal or intracavitary portion, an operating unit 2 connected to the proximal end of the catheter portion 1, and a universal cable 3 having one end thereof connected to the operating unit 2 and the other end detachably connected to the control unit C. The control unit C is constituted by a video signal processor P and a light source L. The catheter portion 1 of the endoscope S is provided with an illumination window and an observation window at the tip end thereof. A light guide which transmits illumination light from the light source is extended through the catheter portion 1 with its light emitting end located in the illumination window, and an objective lens is fitted in the observation window to form an optical image on a solid-state image sensor element like CCD which is located in the imaging plane of the objective lens. These arrangements are well known in the art and therefore omitted in the drawings and in the following description.

The light guide and the cable from the solid-state image sensor element are led through the catheter portion 1 of the endoscope S and through the universal cable 3 via the operating unit 2. The universal cable 3 is provided with an electric connector 3a and an optical connector 3b at its bifurcated ends to be detachably coupled with the video signal processor P and the light source L of the control unit C, respectively. For this purpose, an electric connector socket 4a and an optical connector socket 4b are provided on the part of the control unit C for coupling engagement with the electric connector 3a and the optical connector 3b, respectively.

Figure 2:
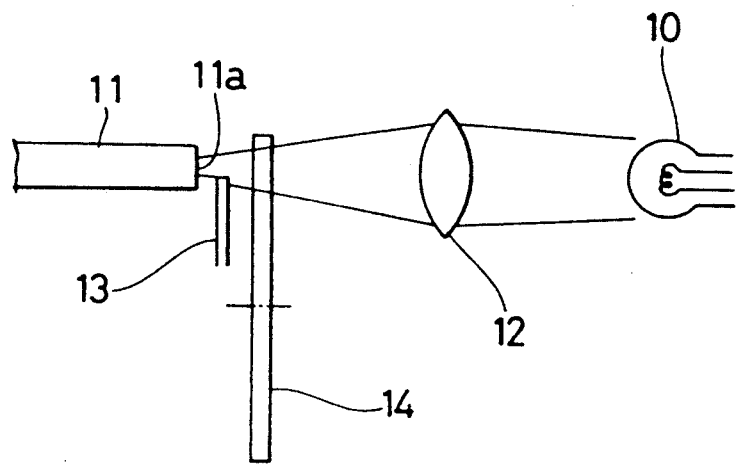
FIG. 2 is a schematic view of a light source, showing its internal arrangement.

As seen in FIG. 2, the light source L which is built in the control unit C includes a source lamp 10 and a condenser lens 12 which is located in the path of illuminating light from the source lamp 10 to converge same toward the light guide 11. For the purpose of adjusting the intensity of illuminating light depending upon the position of a subject of observation, for example, an iris member 13 is interposed between the source lamp 10 and the condenser lens 12. Further, a rotary color wheel 14 is located in a position between the condenser lens 12 and input end 11a of the light guide 11.

Figure 3:
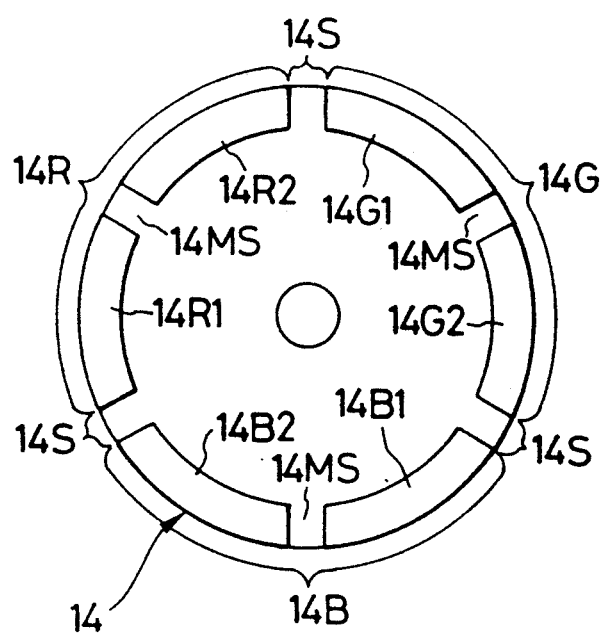
FIG. 3 is a schematic view of a color wheel.

As shown in FIG. 3, the color wheel 14 is provided with an R-filter zone 14R transmissive of light rays of red (R) wavelength, a G-filter zone 14G transmissive of light rays of green (G) wavelength and a B-filter zone 14B transmissive of light rays of blue (B) wavelength successively at predetermined uniform angular intervals (or at angular intervals as determined by RGB sensitivity characteristics) and alternately with a light blocking zone 14S. This color wheel 14 is rotationally driven from a drive means such as an electric motor or the like to direct to the light guide 11 illumination light rays of RGB wavelengths successively through the filter zones 14R, 14G and 14B which are separated by the light-blocking zones 14S. According to the invention, the filter zones 14R, 14G and 14B of the color wheel 14 are bisected into uniform halves 14R1 and 14R2, 14G1 and 14G2, and 14B1 and 14B2, respectively, by intermediate light-blocking zones 14MS which are provided in intermediate portions of the respective filter zones. Accordingly, as the color wheel 14 is turned, the light rays of R, G and B wavelengths are each irradiated twice in the respective irradiation periods for predetermined time durations. Each light-blocking zone 14S which intervenes between irradiation periods of different colors forms a color-shifting light-blocking zone across which a shift in color of illuminating light takes place, while each intermediate light-blocking zone 14MS forms a non-color-shifting light-blocking zone across which no shift in color takes place.

In case of the normal sensitivity (single-field drive type) solid-state image sensor element which is currently used for electronic endoscopes in general, it is necessary to effect an exposure of about 16.6 ms in each irradiation period to obtain the picture data of the corresponding color on every revolution of the color wheel 14. On the other hand, in case of the recently developed high-sensitivity (double-field drive type) solid-state image sensor elements which require only about a half exposure time for obtaining the necessary picture data of each color, it is possible to reduce the number of pixels in the image area to secure a resolution equivalent to that of the above-mentioned normal sensitivity image sensor element, namely, to halve the number of pixels in the vertical direction of the image area to obtain picture images of practically acceptable quality. With a high sensitivity solid-state image sensor element of this sort, the duration of each exposure may be about half of that of the normal sensitivity element, but it becomes necessary to obtain two fields of color data within a period of 16.6 ms.

Figure 6:
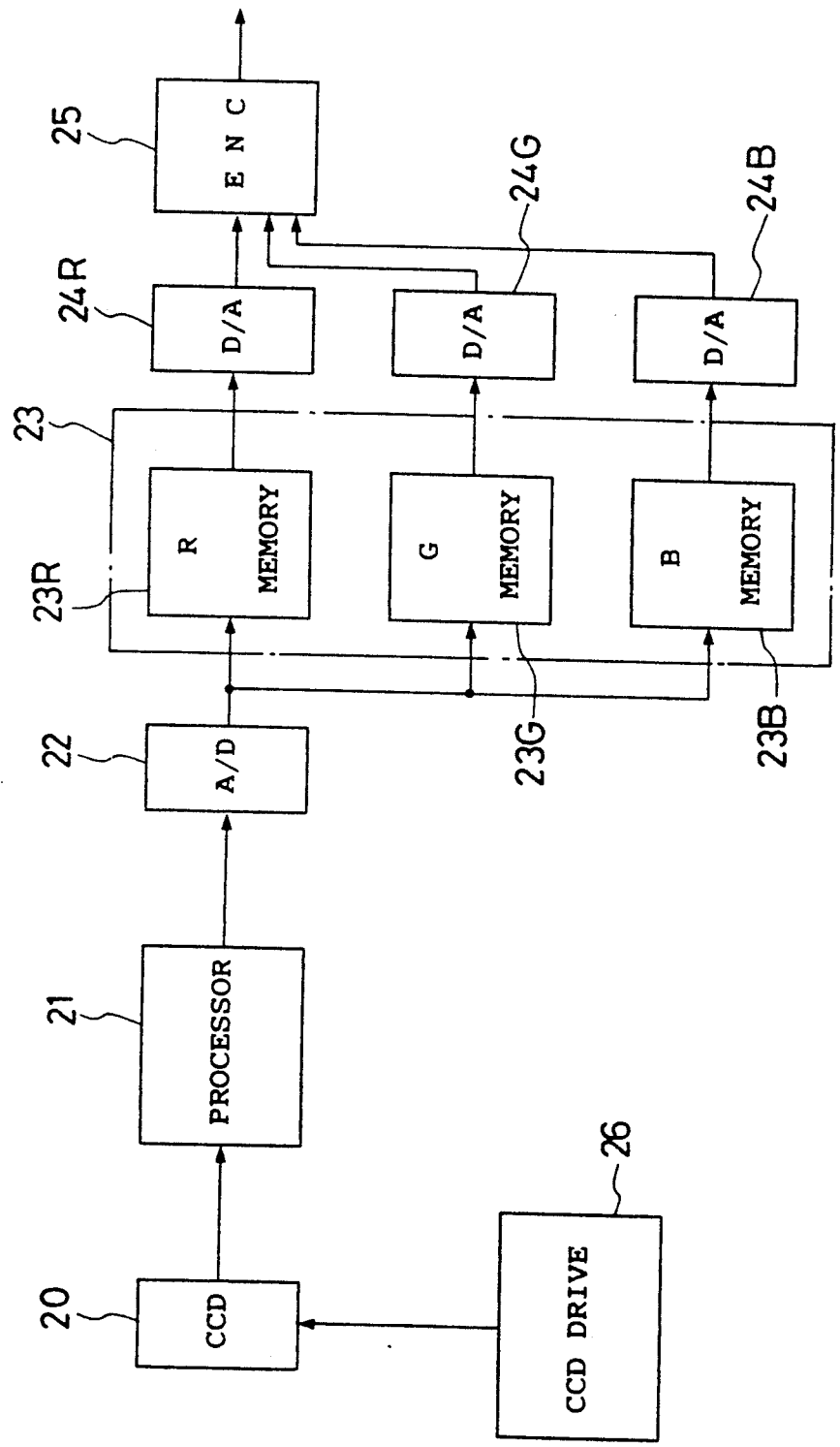
FIG. 6 is a circuit diagram of a video signal processing unit for the single-field drive type solid-state image sensor element.

Therefore, when using a normal sensitivity solid-state image sensor element 20, one field of picture data of each color is acquired during one revolution of the color wheel 14, and the resulting RGB field signals are sent to a signal processing circuit as shown in FIG. 6 to undergo signal processing there. On the other hand, in case of a high-sensitivity solid-state image sensor element 30, two fields of picture data of each color are acquired from the image sensor element during one revolution of the color wheel 14, and the resulting RGB field signals are sent to a signal processing circuit as shown in FIG. 7 to undergo signal processing there.

Thus, in case of the normal sensitivity or single-field drive type solid-state image sensor element 20, it is exposed in each of full irradiation periods RT, GT and BT of RGB wavelengths as shown in FIG. 4(a). The resulting picture signals are shifted to the storage portions during each blank period BL when a color-shifting light-blocking zone 14S is in the illumination light path, and transferred to the video processor 21 which processes the respective signals through predetermined stages including signal clamping, RGB gain adjustment, γ correction, enhancement etc. As a result, RGB picture signals are sequentially produced at the output of the video processor 21. In this instance, as shown at (b) of FIG. 4, the accumulation of signal charges does not take place in the intermediate blank period BM which is provided in each of the RGB irradiation periods RT, GT and BT without a color shift thereacross. This intermediate blank period causes no problems except for the reduction of the integration time. However, a drop of sensitivity which might result from the shortened integration time can be easily corrected, for example, by increasing the intensity of illuminating light.

The output signals from the solid-state image sensor element 20 are converted into digital signals through A/D converter 22, and sequentially written in R-memory 23R, G-memory 23G and B-memory 23B of a memory circuit 23. As soon as the picture data of the respective colors are written in up to one frame, they are simultaneously read out through D/A converters 24R, 24G and 24B and converted into simultaneous signals through the color encoder 25 to produce a composite video signal such as NTSC video signal or the like. In an actual operation, as shown at (c) of FIG. 4, each time the signals read out to the color encoder 25 are renewed with respect to the picture data of one color, R or G or B, and the picture data of the other two colors are same as the data of the previous field. Further, as shown at (d) of FIG. 4, the composite video signal produced by the color encoder 25 consists of combinations of the color signals shown at (c) of FIG. 4.

In this manner, the solid-state image sensor element 20 is exposed in the respective full irradiation periods RT, GT and BT, and the resulting signal charges are read out in the intervening blank periods BL across which a color shift of illuminating light takes place. In this connection, the image sensor element 20 is driven to read out the signal charges according to pulse signals supplied from an image sensor drive circuit 26, which is arranged not to supply a read-out drive signal to the solid-state image sensor element 20 at the intermediate blank periods BM where no shift in color occurs.

On the other hand, in case of the high sensitivity or double-field drive type solid-state image sensor element 30 of reduced size, which is halved in the number of pixels in the vertical direction of the image area, the signals are processed in a different way from the above-described normal sensitivity solid-state image sensor element 20, using a video processor 31 as shown in FIG. 7. More specifically, in this case the high sensitivity solid-state image sensor element 30 is driven to read out signal charges not only in the color-shifting main blank periods BL intervening the full irradiation periods RT, GT and BT but also in the intermediate blank periods BM where no shift in color occurs to illuminating light. Accordingly, as shown in FIG. 5(a), during one revolution of the color wheel 14, the signal charges are read out six times in total, that is, in each of the main blank periods BL and intermediate blank periods BM which intervene the halved irradiation periods RP1, RP2, GP1, GP2, BP1 and BP2, providing two fields of picture data for each color on each revolution. Therefore, in this case, on the basis of the signals from the high sensitivity image sensor element 30, the video processor 31 produces output signals which contain odd-numbered and even-numbered fields of R, G and B picture data as shown at (b) of FIG. 5 within a period corresponding to one field of color data from the normal sensitivity image sensor element 20. After conversion into digital signals through A/D converter 32, these two fields of color data are stored in odd-field memories 33RO, 33GO and 33BO and even-field memories 33RE, 33GE and 33BE (the even- and odd-field memories being divided by address and not necessarily physically separated from each other in actual applications) of RGB memories 33R, 33G and 33B of memory circuit 33. In each frame, one field of the color data in these memories 33R, 33G and 33B is renewed in the same manner as in the case of the normal sensitivity solid-state image sensor element 20.

However, when reading out the field color data in the memory circuit 33 to a color encoder 35 through A/D converters 34R, 34G and 34B, the contents of the odd-field memory and the even-field memory are alternately accessed. Consequently, the picture data of the respective colors are simultaneously read out to the color encoder 35 through D/A converters 34R, 34G and 34B as shown at (c) of FIG. 5, obtaining composite video signals of odd- and even-numbered fields as shown at (d) of FIG. 5.

For reading out the accumulated signal charges, the solid-state image sensor element 30 is driven by pulse signals from the image sensor drive circuit 36 which is arranged to apply a drive signal to the image sensor element 30 not only at every blank period BL but also at every intermediate blank period BM, different from the image sensor drive circuit 26 for the normal sensitivity solid-state image sensor element 20.

With the foregoing arrangements, by simply controlling the image sensor drive to produce or not to produce a drive signal to a solid-state image sensor element at the intermediate light blocking zone 14MS, it becomes possible to use the light source of an electronic endoscope system commonly for both of the normal sensitivity image sensor element 20 and the high sensitivity image sensor element 30 which require different drive systems.

Shown in FIG. 8 is a control unit C which is compatible with an endoscope S' incorporating the normal sensitivity image sensor element 20 as well as an endoscope S" incorporating the high sensitivity image sensor element 30, the control unit C employing a signal processing circuit which is capable of handling video data from both of the solid-state image sensor elements 20 and 30 of different classes.

As shown in that figure, due to a difference in clamp pulse width, there have to be provided a couple of video processors for handling the output signals of the solid-state image sensor elements 20 and 30 of different classes. Therefore, in this embodiment video processors 40a and 40b are provided for the normal sensitivity image sensor element 20 and the high sensitivity image sensor element 30, respectively. These video processors 40a and 40b are each selectively connectable through an input switch 41. An output switch 42 is connected to the output stages of the video processors 40a and 40b to forward the data from the video processor 40a or 40b through A/D converter 43, writing the data in the RGB memories 44R, 44G and 44B of the memory circuit 44. The data which have been written in the respective memories 44R, 44G and 44B are simultaneously read out through D/A converters 45R, 45G and 45B to the color encoder 46 to obtain a composite video signal.

In this manner, the video processor of the image pickup system needs to be changed depending upon the type of the solid image sensor element. However, in the image reproducing system, despite the difference in the read-out control between the normal sensitivity image sensor element 20 and the high sensitivity image sensor element 30, the circuit arrangements, including A/D converter 43, memory circuit 44, D/A converters 45R, 45G and 45B, and color encoder 46, can be commonly used for the two image sensor elements of different classes. Besides, it suffices to provide one master clock circuit 47 which generates clock pulses for the control of the whole signal processing circuit.

The image pickup system, which employs the video processor 40a and 40b exclusively for the respective image sensor elements, needs different clock pulses at the time of writing the output signals of the video processor 40a and 40b in the memory circuit 44. Therefore, its control means 48 is required to be able to switch the control signals between a first mode for controlling the normal sensitivity image sensor element 20 and a second mode for controlling the high sensitivity image sensor element 30. Besides, in the display system which produces composite signals on the basis of the signals read out from the memory 44, its control means 49 is required to be able to switch its control signals between a first mode for the normal sensitivity image sensor element 20 and a second mode for the high sensitivity image sensor element 30. The CCD drive circuit 50 is also arranged to produce two kinds of pulse signals on the basis of clock signals from the master clock circuit 47, namely, a single-field drive pulse signal for skipping the read-out of signal charges at the intermediate blank periods without a shift in color, and a double-field drive pulse signal for reading out signal charges not only at the main blank periods LB with a shift in color but also at the intermediate blank periods BN without a shift in color. Namely, the control means 48 and 49 and CCD drive circuit 50 are switchable between a single-field drive mode for the normal sensitivity image sensor element 20 and a double-field drive mode for the high sensitivity image sensor element 30 according to a signal from an ID decoder 51.

The electronic endoscope system according to invention preferably further includes an ID (identification) mechanism for automatically detecting the type of the endoscope which is connected to the control unit C, that is, the endoscope S' with the single-field drive type image sensor element 20 or the endoscope S" with the double-field drive type image sensor element 30. This ID mechanism is constituted by an ID member in the form of an ID pin which is provided on the electric connector 3a of the universal cable 3 of the endoscope, and an ID decoder 51 which is provided on the part of the control unit C. As the type of a connected endoscope is detected by the ID decoder 51, the control means 48 and 49 and the image sensor drive circuit 50 of the image pickup system and video monitor system are switched to the corresponding operation mode by an ID signal from the decoder 51, setting the respective systems in the single-field drive mode for the normal sensitivity image sensor element 20 or in the double-field drive mode for the high sensitivity image sensor element 30.

Accordingly, when the endoscope S' with the image sensor element 20 of the single-field drive type is connected to the control unit C, the control means 48 and 49 and the CCD drive circuit 50 are set in the single-field drive mode in response to a corresponding ID signal from the ID decoder 51. On the other hand, when the endoscope S" with the image sensor element 30 of the double-field drive type is connected to the control unit C, the control means 48 and 49 and the CCD drive circuit 50 are set in the double-field drive mode in response to a corresponding ID signal from the ID decoder 51.

With the foregoing circuit arrangement, the control unit C which incorporates a light source integrally with a video signal processing circuit can be used commonly for an endoscope S' with an image sensor element 20 of the single-field drive type and an endoscope S" with an image sensor element 30 of the double-field drive type, automatically setting the operation in the mode for the endoscope S' or S" when the latter is connected to the control unit.

What is claimed is:

1. An electronic endoscope system, comprising:
   an illumination lamp;
   a rotary color wheel located in the path of illuminating light from said illumination lamp and formed with RGB filter zones successively and alternately with one of a plurality of color-shifting main light-blocking zone to transmit illuminating light rays of red, green and blue wavelengths sequentially therethrough, and an intermediate light-blocking zone provided at a median point of each one of said RGB filter zones;
   a light guide adapted to guide said illuminating light rays of red, green and blue wavelengths from said color wheel sequentially to a subject under observation;
   a solid-state image sensor element for picking up the image of said subject under sequential irradiations by said red, green and blue light rays from said light guide; and
   an image sensor drive circuit switchable to operate in a single-field drive mode where signal charges are read out from said image sensor element only at each main blank period when said one color-shifting main light-blocking zone is in the path of said illuminating light, skipping over the intermediate light-blocking zones, and in a double-field drive mode where signal charges are read out from said image sensor element at each one of said main and at each one of a plurality of intermediate blank periods when a main and intermediate light-blocking zone is respectively in the path of said illuminating light, thereby obtaining two fields of picture data of each color of said RGB filter zones on each revolution of said color wheel.

2. An electronic endoscope system as defined in claim 1, wherein said solid-state image sensor element is of single-field drive type connected to a memory circuit capable of storing one set of red, green and blue picture data of said subject and driven by said image sensor drive circuit to read out said signal charges at said main blank periods, or of double-field drive type connected to said memory circuit capable of storing two sets of red, green and blue picture data of said subject and driven by said image sensor drive circuit to read out said signal charges at both of said main and intermediate blank periods.

3. An electronic endoscope system as defined in claim 2, wherein said memory circuits are incorporated into a single control unit, said control unit being connectible to an endoscope with said single-field drive type solid-state image sensor element as well as to an endoscope with said double-field drive type solid-state image sensor element.

4. An electronic endoscope system as defined in claim 3, wherein said control unit includes an ID mechanism capable of detecting whether a connected endoscope is of the single-field drive type or the double-field drive type, and switching the operation of said endoscope automatically to said single-field drive mode or said double-field drive mode.

* * * * *